(12) United States Patent
Shin et al.

(10) Patent No.: US 9,753,819 B2
(45) Date of Patent: Sep. 5, 2017

(54) TEST DEVICE AND METHOD FOR CONTROLLING THE SAME

(71) Applicant: SAMSUNG ELECTRONICS CO., LTD., Suwon-si (KR)

(72) Inventors: Im Ho Shin, Suwon-si (KR); Ki Ju Lee, Suwon-si (KR); Jung Tae Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 136 days.

(21) Appl. No.: 14/751,726

(22) Filed: Jun. 26, 2015

(65) Prior Publication Data

US 2016/0132402 A1  May 12, 2016

(30) Foreign Application Priority Data

Nov. 11, 2014 (KR) .................. 10-2014-0156296

(51) Int. Cl.
*G06F 11/00* (2006.01)
*G06F 11/14* (2006.01)
*G01N 35/00* (2006.01)

(52) U.S. Cl.
CPC ... *G06F 11/1471* (2013.01); *G01N 35/00069* (2013.01); *G01N 35/00623* (2013.01); *G01N 35/00712* (2013.01); *G01N 35/00732* (2013.01); *G01N 2035/00633* (2013.01); *G06F 2201/805* (2013.01); *G06F 2201/84* (2013.01)

(58) Field of Classification Search
CPC ....... G01N 35/00069; G01N 35/00623; G01N 35/00712; G06F 11/1402; G06F 11/1433; G06F 11/1438; G06F 11/1441; G06F 11/1446; G06F 11/22; G06F 11/2205; G06F 11/273; G06F 11/2736; G06F 11/36; G06F 11/3664; G06F 11/3668; G06F 2201/805; G06F 2201/84

See application file for complete search history.

(56) References Cited

U.S. PATENT DOCUMENTS

| 4,025,767 A * | 5/1977 | Bottard | G06F 11/2736 714/25 |
| 4,639,916 A * | 1/1987 | Boutterin | G06F 11/273 714/27 |
| 4,933,941 A * | 6/1990 | Eckard | G06F 11/2736 714/31 |
| 5,353,240 A * | 10/1994 | Mallory | G06F 11/273 324/73.1 |

(Continued)

FOREIGN PATENT DOCUMENTS

| KR | 1020000003195 A | 1/2000 |
| KR | 1020020008722 A | 1/2002 |
| KR | 1020050000565 A | 1/2005 |

*Primary Examiner* — Joshua P Lottich
(74) *Attorney, Agent, or Firm* — Sughrue Mion, PLLC

(57) ABSTRACT

A test device and a method for controlling the test device are disclosed. After a test is interrupted due to a malfunction of the test device, the test device continuously performs the interrupted testing. The test device for testing a biological material includes: a memory configured to store information which relates to progress of a test; and a controller which, if the test is interrupted due to a malfunction of the test device, is configured to continue performance of the test by using the information which relates to the test progress which is stored in the memory.

28 Claims, 12 Drawing Sheets

(56) References Cited

U.S. PATENT DOCUMENTS

| | | | | |
|---|---|---|---|---|
| 5,566,303 A * | 10/1996 | Tashiro | G01R 31/31701 | 377/39 |
| 7,809,988 B1 * | 10/2010 | Portal | G06F 11/3664 | 714/35 |
| 8,019,588 B1 * | 9/2011 | Wohlberg | G06F 11/3692 | 703/22 |
| 8,078,448 B1 * | 12/2011 | Wohlberg | G06F 11/3664 | 703/23 |
| 8,626,991 B1 * | 1/2014 | Beauchamp | G06F 12/0246 | 707/693 |
| 2003/0046612 A1 * | 3/2003 | Grey | H04L 1/24 | 714/38.1 |
| 2011/0055632 A1 * | 3/2011 | Zimmerman | G06F 11/2294 | 714/31 |
| 2012/0042213 A1 * | 2/2012 | Zimmerman | H04L 43/12 | 714/46 |
| 2012/0047487 A1 * | 2/2012 | Ambichl | G06F 11/3684 | 717/124 |
| 2012/0151263 A1 * | 6/2012 | Rentschler | G06F 11/22 | 714/30 |
| 2012/0233123 A1 * | 9/2012 | Shisheng | G06F 11/004 | 707/639 |
| 2013/0104106 A1 * | 4/2013 | Brown | G06F 11/3696 | 717/124 |
| 2014/0173569 A1 * | 6/2014 | Krauss | G06F 11/362 | 717/125 |
| 2014/0233743 A1 * | 8/2014 | Hillbratt | G06F 11/22 | 381/60 |
| 2014/0250251 A1 * | 9/2014 | Marks | G06F 9/445 | 710/267 |
| 2014/0297597 A1 * | 10/2014 | Matsubara | G06F 9/461 | 707/681 |
| 2015/0051848 A1 * | 2/2015 | Jurkowitz, Jr. | H04B 7/26 | 702/50 |
| 2015/0278076 A1 * | 10/2015 | BS | G06F 11/3664 | 714/38.1 |
| 2016/0070365 A1 * | 3/2016 | Patwardhan | G06F 3/038 | 345/156 |
| 2016/0072692 A1 * | 3/2016 | Patwardhan | H04L 43/14 | 709/224 |
| 2016/0283356 A1 * | 9/2016 | Waldman | G06F 11/3672 | |

* cited by examiner

TEST DEVICE AND METHOD FOR CONTROLLING THE SAME

CROSS-REFERENCE TO RELATED APPLICATION

This application claims priority from Korean Patent Application No. 10-2014-0156296, filed on Nov. 11, 2014 in the Korean Intellectual Property Office, the disclosure of which is incorporated herein by reference in its entirety.

BACKGROUND

1. Field

Exemplary embodiments relate to a test device for conducting a test for biological materials using a reactor and a method for controlling the same.

2. Description of the Related Art

A microfluidic device is used to perform biological or chemical reactions by manipulating small amounts of fluid.

A microfluidic structure provided in a microfluidic device and configured to perform an independent function generally includes a chamber configured to accommodate a fluid, a channel configured to facilitate a flow of the fluid therethrough, and a member configured to regulate the flow of the fluid. The microfluidic structure may be realized through any of various combinations of such structures. A device fabricated by disposing such a microfluidic structure on a chip-shaped substrate configured to perform multi-step processing and manipulation to conduct a test involving immune serum reaction or biochemical reaction on a small chip is referred to as a lab-on-a chip.

To transfer a fluid in a microfluidic structure, driving pressure is needed. Capillary pressure or pressure generated by a separate pump may be used as the driving pressure. Recently, a disc-type microfluidic device which has a microfluidic structure arranged on a disc-shaped platform and moves a fluid using centrifugal force to perform a series of operations has been proposed. This device is referred to as a Lab CD or Lab-on a CD.

A microfluidic device includes a chamber configured to detect an analyte or test material and a detection object such as test paper.

A test device is an apparatus provided with a light emitting element and a light receiving element configured to detect a detection object of the microfluidic device and thereby detect a result of a biochemical reaction occurring on the detection object, and includes a blood testing device.

SUMMARY

Therefore, it is an aspect of one or more exemplary embodiments to provide a test device which, after a test is interrupted due to a malfunction or faulty operation of the test device, is configured to continuously perform the interrupted testing, and a method for controlling the same.

Additional aspects of the exemplary embodiments will be set forth in part in the description which follows and, in part, will be apparent from the description, or may be learned by practice of the exemplary embodiments.

In accordance with an aspect of one or more exemplary embodiments, a test device for testing a biological material includes: a memory configured to store information which relates to progress of a test; and a controller which, if the test is interrupted due to a malfunction of the test device, is configured to continue a performance of the interrupted test by using the information which relates to the progress of the test which is stored in the memory.

The test device may further include: an auxiliary power supplier configured to provide the test device with auxiliary power when the test device is powered off.

The memory may be further configured such that if the test device is powered off so that the test is interrupted, the information stored in the memory includes information which relates to a test step of a specific time at which the test is interrupted, by using power received from the auxiliary power supplier.

If a rebooting command is received, the controller may be further configured to reboot the test device, and to continue the performance of the interrupted test by using the information which relates to the test step of the specific time at which the test is interrupted.

The controller may be further configured to continue the performance of the interrupted test during a test time calculated when a time consumed for rebooting is subtracted from a remaining test time.

After the test device is rebooted, the controller may be further configured to determine whether the interrupted test step is a test step which is capable of being resumed, and to display a message for confirming whether the interrupted test step is to be resumed on a display of the test device, when the interrupted test step is not identical to the test step which is determined as being capable of being resumed.

If a resume command with respect to the interrupted test step is received in response to the message, the controller may be further configured to continue the performance of the interrupted test by using the stored information which relates to the test step at a test stoppage time point.

When a predetermined test step is completed, the memory may be further configured to store information which relates to the completed test step.

If the test device is interrupted and a predetermined time elapses after the interruption, the controller may be further configured to reboot the test device, and to perform steps starting from a previously completed test step which was completed prior to the interruption of the test device, by using the information stored in the memory.

After the test device is rebooted, the controller may be further configured to determine whether the interrupted test step is a test step which is capable of being resumed, and to display a message for confirming whether the interrupted test step is to be resumed on a display of the test device, when the interrupted test step is not identical to the test step which is determined as being capable of being resumed.

If a resume command with respect to the interrupted test step is received in response to the message, the controller may be further configured to perform steps starting from a previously completed test step which was completed prior to the interruption of the test device by using the information stored in the memory.

In accordance with another aspect of one or more exemplary embodiments, a method for controlling a test device configured to perform a test of a biological material includes: if a test is interrupted due to a malfunction of the test device, storing information which relates to progress of the test; and continuing a performance of the interrupted test by using the stored information.

The storing the information which relates to the test progress may include: if the test device is powered off so that the test is interrupted, storing information which relates to a test step of a specific time at which the test is interrupted, by using power received from an auxiliary power supplier.

The method may further include: rebooting the test device in response to a rebooting command; determining whether the interrupted test step is a test step which is capable of being resumed; and if the interrupted test step is not identical to the test step which is determined as being capable of being resumed, displaying a message for confirming whether the interrupted test step is to be resumed, on a display of the test device.

The method may further include: if a resume command with respect to the interrupted test step is received in response to the message, continuing the performance of the interrupted test by using the stored information which relates to the test step at a test stoppage time point.

The operation for continuing the performance of the interrupted test may include: continuing the performance of the interrupted test during a test time calculated when a time consumed for rebooting is subtracted from a remaining test time.

The operation for continuing the performance of the interrupted test may include: continuing the performance of the interrupted test by using the information which relates to the test step at a test stoppage time point.

The storing the information which relates to the test progress may include: when a predetermined test step is completed, storing information which relates to the completed test step.

The method may further include: determining whether a predetermined time has elapsed after the test device was interrupted; rebooting the test device if the predetermined time has been determined as having elapsed; determining whether the interrupted test step is a test step which is capable of being resumed; and if the interrupted test step is not identical to the test step which has been determined as being capable of being resumed, displaying a message for confirming whether the interrupted test step is to be resumed on a display of the test device.

If a resume command with respect to the interrupted test step is received in response to the message, the method may further include performing steps starting from a previously completed test step which was completed prior to the interruption of the test device by using the information stored in the memory.

The operation for continuing the performance of the interrupted test may include: continuing the performance of the interrupted test during a test time calculated when a time consumed for rebooting is subtracted from a remaining test time.

The operation for continuing the performance of the interrupted test may include: performing steps starting from a previously completed test step which was completed prior to the interruption of the test device by using the stored information.

In accordance with another aspect of one or more exemplary embodiments, a non-transitory computer-readable recording medium comprising a program configured to execute a control method of the test device.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
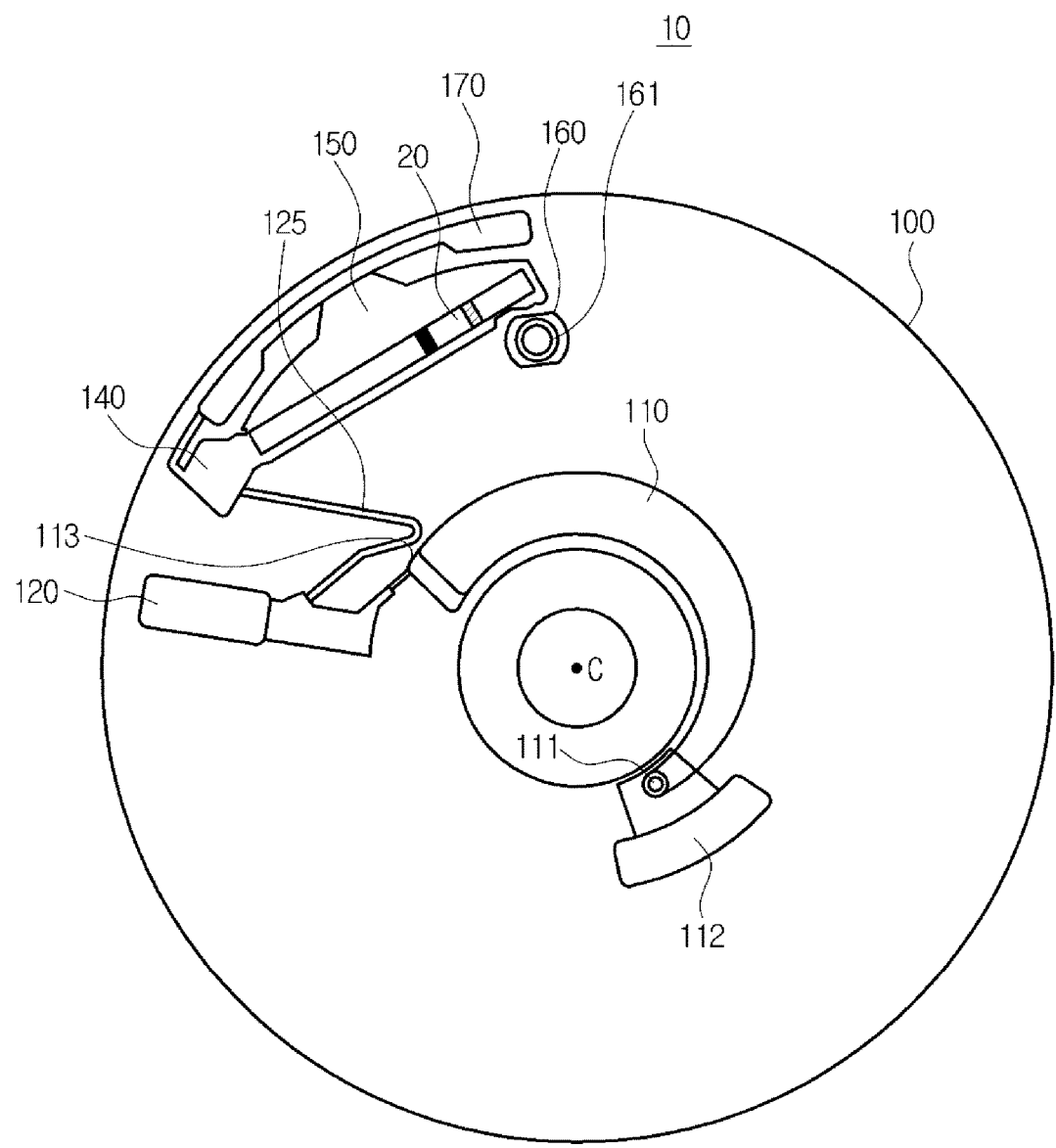
FIG. 1 is a schematic view illustrating a disc-type reactor, according to an exemplary embodiment.

Reference will now be made in detail to exemplary embodiments, examples of which are illustrated in the accompanying drawings, wherein like reference numerals refer to like elements throughout.

FIG. 1 is a schematic view illustrating a disc-type reactor, according to an exemplary embodiment.

Referring to FIG. 1, the microfluidic device 10 includes a platform 100 on which a microfluidic structure is formed and microfluidic structures formed thereon.

The microfluidic structure includes a plurality of chambers configured to accommodate a fluid and a channel configured to connect the chambers.

Here, the microfluidic structure is not limited to a structure with a specific shape, but comprehensively refers to structures, including the channel connecting the chambers to each other, formed on the reactor 10, especially on the platform of the reactor 10, and configured to facilitate a flow of fluid. The microfluidic structure may perform various functions depending on arrangements of the chambers and the channel and the kind of the fluid accommodated in the chambers or flowing through the channel.

The platform 100 may be made of any of various materials, including plastic materials, such as, for example, polymethylmethacrylate (PMMA), polydimethylsiloxane (PDMS), polycarbonate (PC), polypropylene, polyvinyl alcohol and polyethylene, glass, mica, silica and silicon wafer which are easy to work with and whose surfaces are biologically inactive. The above materials are simply examples of materials usable for the platform 100, and exemplary embodiments are not limited thereto. Any material having proper chemical and biological stability, optical transparency and mechanical workability may be used as a material of the platform 100.

The platform 100 may be formed in multiple layers of plates. A space configured to accommodate a fluid in the platform 100 and a channel configured to facilitate a flow of the fluid therethrough may be provided by forming intaglio structures corresponding to the microfluidic structures such as the chambers and the channel on the contact surfaces of two plates and joining the plates. Joining two plates may be implemented using any of various techniques, such as binding with an adhesive agent or a double-sided adhesive tape, ultrasonic welding and laser welding.

The illustrated exemplary embodiment of FIG. 1 employs a circular plate-shaped disc type platform 100, but the platform 100 used in the illustrated exemplary embodiment may have the shape of a whole circular plate which is rotatable or a circular sector rotatable in a rotatable frame when seated thereon, or may have any polygonal shape provided that such shape is rotatable by power.

The reactor 10 according to one exemplary embodiment causes the fluid to move by using centrifugal force, the chamber configured to receive the fluid is disposed at a position more distant from the center of the platform 100 than the position of the other chamber configured to supply the fluid, as shown in FIG. 1.

The sample supply chamber 110 is formed at a position which is relatively close to the center of rotation C in order to accommodate a sample supplied from the outside. The sample supply chamber 110 accommodates a fluidic sample, and in the illustrated exemplary embodiment, the sample supplied is blood.

A sample introduction inlet 111 is provided at one side of the sample supply chamber 110, and an instrument, such as a pipette, may be used to introduce blood into the sample supply chamber 110 via the sample introduction inlet 111. Blood may be spilled near the sample introduction inlet 111 during the introduction of blood, or the blood may flow backward via the sample introduction inlet 111 during rotation of the platform 100. To prevent the reactor 10 from being contaminated by such events, a backflow receiving chamber 112 may be formed on the upper surface of the reactor 10 adjacent to the sample introduction inlet 111 in order to accommodate the blood spilled during the introduction thereof or the blood flowing backward.

In another exemplary embodiment, in order to prevent backflow of the blood introduced into the sample supply chamber 110, a structure which functions as a capillary valve configured to allow passage of a sample only when a pressure greater than or equal to a predetermined level is applied may be formed in the sample supply chamber 110.

In a further exemplary embodiment to prevent backflow of the blood introduced into the sample supply chamber 110, a rib-shaped backflow prevention device may be formed in the sample supply chamber 110. Arranging the backflow prevention device in a direction which crosses the direction of flow of the sample from the sample introduction inlet 111 to the sample discharge outlet may produce resistance to flow of the sample, thereby preventing the sample from flowing toward the sample introduction inlet 111.

The sample supply chamber 110 may be formed to have a width which gradually increases from the sample introduction inlet 111 to the sample discharge outlet 113 in order to facilitate discharge of the sample accommodated therein through the sample discharge outlet 113.

The sample discharge outlet 113 of the sample supply chamber 110 is connected to the first chamber 120. Although not shown in the drawing, the sample discharge outlet 113 may be connected to the distribution channel formed on the platform 100 in the circumferential direction of the platform 100, and the distribution channel may be sequentially connected to at least one first chamber. Although the distribution channel 115 is omitted from the drawing illustrated as FIG. 1, one first chamber 120 and one second chamber 130 connected to this first chamber 120 are shown for convenience of description and better understanding of the present exemplary embodiment, it should be noted that at least two first chambers and at least two second chamber may be arranged in a parallel manner in the circumferential direction along the distribution channel.

The first chambers 120 may accommodate the sample supplied from the sample supply chamber 110 and cause the sample to separate into supernatant and sediment through centrifugal force. Since the sample used in this exemplary embodiment is blood, the blood may separate into the supernatant including serum and plasma and sediment including corpuscles in the first chambers 120.

A siphon channel 125 may be connected to the first chamber 120. The siphon channel refers to a channel which causes a fluid to move by using pressure differential. In the disc-type reactor 10, the flow of the fluid through the siphon channel is controlled by using capillary pressure that forces the fluid to move up through a tube having a very small cross-sectional area and centrifugal force generated by rotation of the platform 100. In particular, the inlet of the siphon channel having a very small cross-sectional area is connected to the chamber in which the fluid is accommodated, and the outlet of the siphon channel is connected to another chamber to which the fluid is transferred. Here, a point at which the siphon channel is bent, i.e., the highest point of the siphon channel should be higher than the level of the fluid accommodated in the chamber. When the siphon channel is filled with the fluid by the capillary pressure of the siphon channel, the fluid filling the siphon channel is transferred to the next chamber by centrifugal force.

In addition, the position at which the inlet of the siphon channel 125 meets the outlet of the first chamber 120 depends on the amount of the fluid to be transferred. If the sample is blood, only supernatant may be tested, so that an outlet may be provided over the first chamber 120 which includes supernatant. A protrusion portion for facilitating movement of the fluid is provided at the outlet of the first chamber 120, so that the first chamber 120 may be connected to the siphon channel 125. However, the scope or spirit of the present inventive concept is not limited thereto, if the sample is not identical to the blood or if the sample is the blood and the sediment is further tested, an outlet may be provided below the first chamber 120.

The outlet of the siphon channel 125 may be connected to the second chamber 140, and the second chamber 140 may be implemented as a metering chamber according to this exemplary embodiment. The metering chamber 140 may function to meter a fixed amount of blood accommodated in the chamber and supply the fixed amount of blood to the reactor 150.

The residue in the metering chambers 140 which has not been supplied to the reactor 150 may be transferred to waste chambers 170.

The second chamber 140 is coupled to the reactor 150. The reactor 150 may be implemented as chambers, such as, for example, first and second chambers, and the reactor 150 may include a strip 20 which is capable of detecting a presence or absence of a target material to be analyzed by chromatography. Although the strip is contained in the reactor as shown in FIG. 1, the scope or spirit of the present inventive concept is not limited thereto, the reactor may include any of various kinds of reagents for detecting a desired detection object by performing biochemical reactions with a sample instead of the strip. The case in which the strip is contained in the reactor will hereinafter be described in detail.

The strip 20 may include a reaction paper that is formed by one selected from among a thin porous film (membrane) such as cellulose, a micropore, and a micro-pillar, upon which capillary pressure acts. When a biosample, such as blood or urine, is dropped on the reaction paper 20, the biosample moves due to capillary pressure. When the biosample flowing according to the capillary pressure reaches the test line, a material configured for capturing the biosample provided at the test line is combined with the biosample so as to form a sandwich combination. Therefore, if analyte is contained in the biosample, it may be detected by the marker on the test line.

The platform 100 may be provided with a magnetic-body accommodating chamber 160 which is configured for position identification. A magnetic body 161 is accommodated in the magnetic-body accommodating chamber 160. The magnetic body 161 contained in the magnetic-body accommodating chamber 160 may be formed of a ferromagnetic material such as iron, cobalt, and/or nickel, which have a high intensity of magnetization and form a strong magnet like a permanent magnet, or may alternatively be formed of a paramagnetic material such as chromium, platinum, manganese, and/or aluminum which have a low intensity of magnetization and thus do not form a magnet in isolation, but may become a magnet when a magnet approaches thereto to increase the intensity of magnetization.

Although not shown in the drawing, the reactor 10 may include a tag configured for identifying the reactor 10 and having information regarding a method for testing the reactor 10. The tag may include a one-dimensional (1D) barcode, a two-dimensional (2D) barcode such as a quick response (QR) code, or a radio frequency identification (RFID) code. The tag may be attached on a disc without using a separate container, and the detection module 59 of the test device may identify the reactor 10 by reading the tag and thus decide the testing method. If the tag is an RFID tag, the detection module 59 may include an RFID reader.

The tag may include identification (ID) information of the reactor 10 called a disc through which the corresponding reactor 10 detects one test item using the detection result of several reactor units 150, or may include ID information of the reactor 10 called a disc through which the corresponding reactor 10 can detect different detection items. If the disc is used to detect one test item using the detection result of several reactor units 150, information regarding a test method for calculating one test item using the detection result of several reactor units 150 may be contained in the tag.

Figure 2:
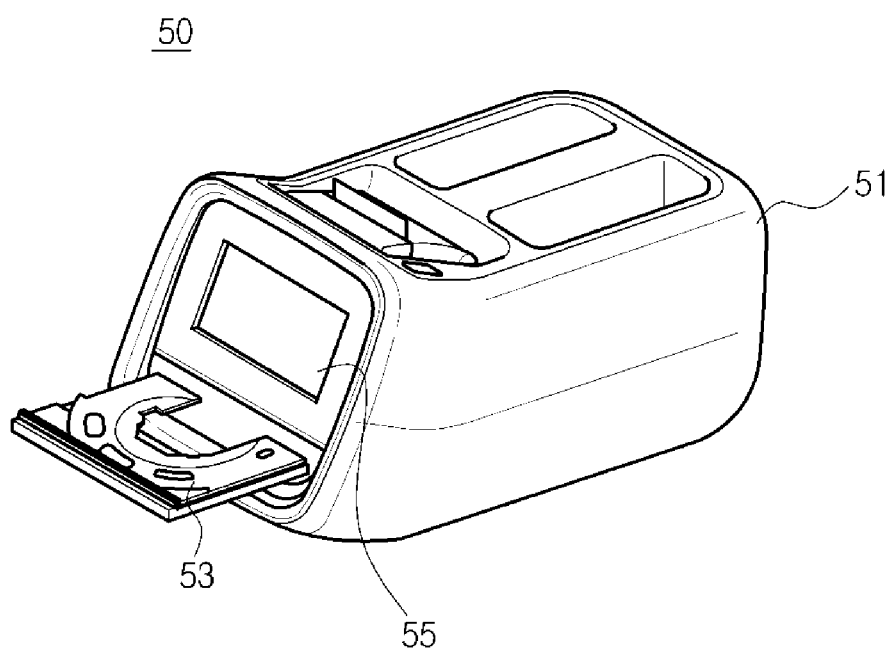
FIG. 2 illustrates the external appearance of a test device configured to test a disc-type reactor, according to an exemplary embodiment.
Figure 3:
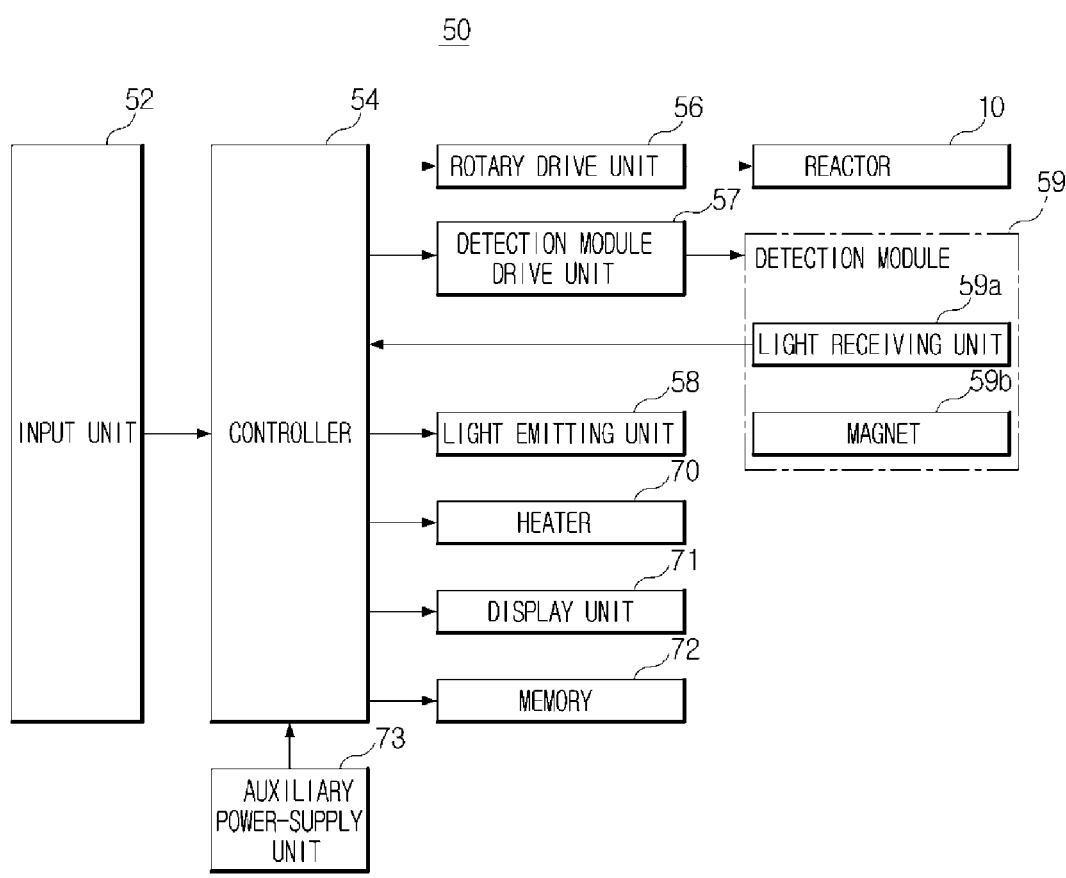
FIG. 3 is a block diagram illustrating a test device, according to an exemplary embodiment.
Figure 4:
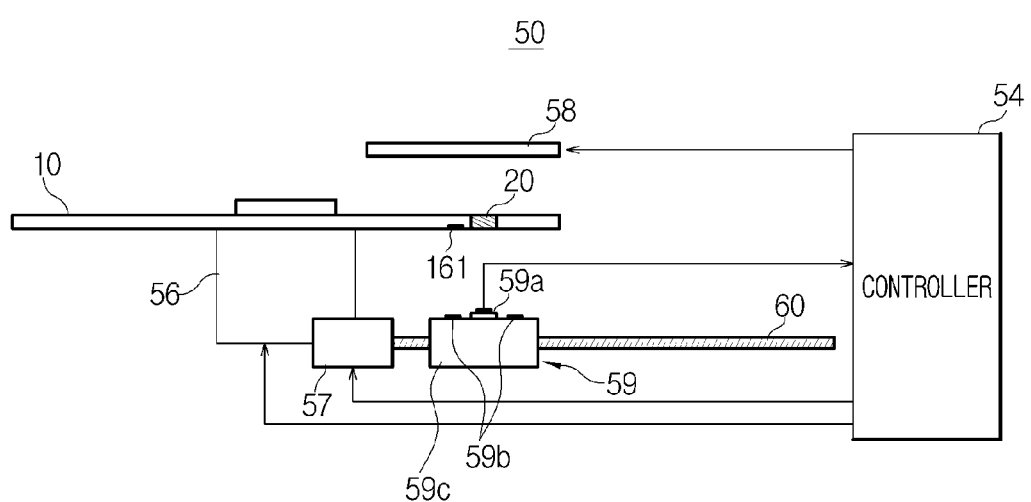
FIG. 4 is a conceptual lateral view illustrating a test device, according to an exemplary embodiment.
Figure 5:
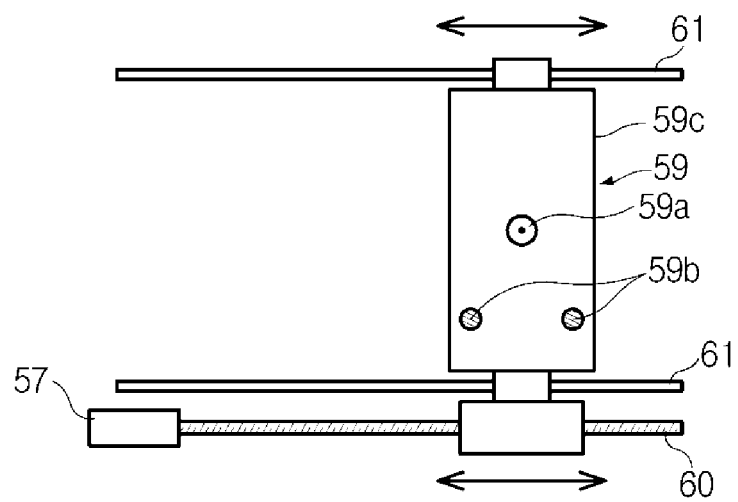
FIG. 5 is a top view illustrating a detection module which is movable in a radial direction.

FIG. 2 illustrates the external appearance of a test device configured to test the disc-type reactor 10, according to an exemplary embodiment. FIG. 3 is a block diagram illustrating the test device, according to an exemplary embodiment. FIG. 4 is a conceptual lateral view illustrating the test device, according to an exemplary embodiment. FIG. 5 is a top view illustrating a detection module 59 which is movable in a radial direction.

Referring to FIG. 2, if the disc-type reactor 10 in which the sample is implanted is loaded on a tray 53 contained in the test device 50, and the tray is inserted into the main body 51 of the test device 50, the test device 50 may rotate the reactor 10 in order to perform a test.

If the sample or reagent moves along respective chambers and channels by centrifugal force in response to rotation of the reactor 10, and thus a reaction occurs in the reaction unit 150, the reactor 10 may facilitate a movement of the detection module 59 to a specific position corresponding to the reaction unit 150, and thusly may detect the reaction result generated in the reaction unit 150. If the test is completed, the detection result of the test item is displayed on the display unit (also referred to herein as a "display") 55 in such a manner that a user can recognize the detection result.

Referring to FIG. 3, the test device 50 may include a rotary drive unit (also referred to herein as a "rotary driver") 56 configured to rotate the reactor 10; a light emitting unit (also referred to herein as a "light emitter") 58 configured to emit light to the reactor 10; a detection module 59 provided with a light receiving unit (also referred to herein as a "light receiver") 59*a* which reads a tag of the reactor 10 through the light emitted from the light emitting unit 58 or detects the reaction paper 20 contained in the reaction unit 150; a detection module drive unit (also referred to herein as a "detection module driver") 57 configured to move the detection module 59 in a radial direction; a heater 70 configured to maintain or adjust a predetermined temperature of a space including the reactor; a display unit (also referred to herein as a "display device" and/or as a "display") 71 configured to provide information related to a test progress; a memory 72 configured to store information related to a test progress; an auxiliary power-supply unit (also referred to herein as an "auxiliary power supplier" and/or as an "auxiliary power supply") 73 configured to provide auxiliary power in such a manner that the memory can store information related to a test step when powered off; an input unit (also referred to herein as an "input device") 52 configured to enable a user to input a command therethrough from the outside; and a controller 54 configured to control overall operations and functions of the test device 50 according to the commands received via the input unit 52.

The rotary drive unit 56 may be realized with a spindle motor. If the reactor 10 is loaded, the rotary drive unit 56 is driven by a control signal of the controller 54 so as to rotate the reactor 10. The rotary drive unit 56 may receive a signal generated from the controller 54 and repeat the operation of rotation and stop, so that the tag on the reactor 10 or the reaction paper 20 may move to desired positions.

The light emitting unit 58 may include a surface light source having a large light emitting area so as to uniformly emit light to a certain region of the reactor 10. For example, a back light unit and/or a backlight device may be used as the light emitting unit 58.

The light emitting unit 58 may be arranged to face the same direction as the light receiving unit 59*a*, or it may be arranged to face the light receiving unit 59*a*, as shown in FIG. 4. FIG. 4 shows that the light emitting unit 58 is positioned at the upper side of the reactor 10 and the light receiving unit 59*a* is positioned at the lower side of the reactor 10 such that the reactor 10 is placed between the light emitting unit 58 and the light receiving unit 59*a*. However, the positions of the light emitting unit 58 and the light receiving unit 59*a* may be varied. The light emitting unit 58 may be controlled by the controller 54 so as to adjust the amount of light emitted therefrom.

The light receiving unit 59*a* receives light reflected from or transmitted through the tag or the reaction paper 20 after being emitted from the light emitting unit 58, and reads the tag or detects the reaction paper 20. The light receiving unit 59*a* may include a complementary metal-oxide-semiconductor (CMOS) image sensor and/or a charge-coupled device (CCD) image sensor.

When the light receiving unit 59*a* receives light which has reflected from or propagated through the tag or the reaction paper 20 and obtains an image of the tag or the reaction paper 20, the controller 54 obtains information stored in the tag via the image, and detects the concentration of the analyte based on a concentration of the test line 21 of the reaction paper 20.

The test device 50 according to this exemplary embodiment has one light receiving unit 59*a* installed at the detection module 59, which is a mechanism that is moveable in a radial direction, such that the light receiving unit 59a may detect the tag and a plurality of reaction papers 20 provided in the reactor 10.

Referring to FIG. 5, the detection module 59 may be moved in a radial direction by driving force supplied from the detection module drive unit 57. The detection module drive unit 57 may include a feeding motor and/or a stepping motor.

The detection module 59 may include a plate 59c on which a constituent, such as the light receiving unit 59a or the magnet 59b, is installed. The detection module 59 may be slidably moved by two guide units 61 which guide stable radial movement. The guide unit 61 may be formed in a rod shape, and the plate 59c may be coupled to the guide unit 61 so as to move along the guide member 61. The plate 59c is slidably mounted on the guide unit 61 to support the detection module 59 and to facilitate a movement of the detection module 59 along the guide unit 61.

Further, the detection module 59 is mounted on a power transmission unit (also referred to herein as a "power transmitter") 60 such that power produced by the detection module drive unit 57 is transmitted to the detection module 59 via the power transmission unit 60 in order to move the detection module 59 in a radial direction. In particular, when the detection module drive unit 57 is actuated and the power thereof is transmitted to the detection module 59 via the power transmission unit 60, the detection module 59 moves along the power transmission unit 60 and the guide unit 61 in a radial direction.

The magnet 59b provided in the detection module 59 applies attractive force the magnetic body 161 of the magnetic body accommodating chamber 160 formed in a region adjacent to the reaction paper 20 or the tag, in order to identify the position of the reaction paper 20 of the reactor 10 or the tag. In this exemplary embodiment, a magnet 59b is accommodated in the detection module 59, and a magnetic material 161 is accommodated in the reactor 10. However, exemplary embodiments are not limited thereto. The magnetic body may be installed into the detection module 59, and the magnet may also be installed into the reactor 10. When the magnet 59b of the detection module 59 and the magnetic body 161 of the reactor 10 face each other, attractive force is applied to the magnetic body 161 by the magnet 59b, and the reactor 10 may stay in place as long as force exceeding the attractive force is applied thereto. When the magnetic body 161 of the reactor 10 is positioned to face the magnet 59b and the position thereof is fixed by the attractive force, the magnet 59b in the detection module 59 is arranged at a position at which the reaction paper 20 faces the light receiving unit 59a of the detection module 59. In particular, when the magnetic body 161 of the reactor 10 and the magnet 59b of the detection module 59 are arranged to face each other, the reaction paper 20 naturally faces the light receiving element 1411. As such, with the magnet 59b installed at the detection module 59, when the magnetic body 161 is moved close to the magnet 59b by rotation of the reactor 10 toward the light receiving unit 59a to detect the reaction paper 20, the magnetic body 161 is fixed by the attractive force of the magnet 59b, and thereby the reactor 10 stops moving, with the reaction paper 20 facing the light receiving unit 59a.

The controller 54 may rotate the reactor 10 by controlling the rotary drive unit 56, control the detection module drive unit 57 in such a manner that the detection module 59 moves in a radial direction, so that the light receiving unit 59a can detect the tag and the reaction unit 150.

If the light receiving unit 59a obtains an image of the tag, the controller 54 may identify the type of the reactor 10 by reading the tag. If the reactor 10 is provided in a manner that individual reaction units 150 can detect different test items, the controller 54 may calculate the detection result of different test items on the basis of the detection result of each reactor 150 detected by the light receiving unit 59a. Alternatively, if a plurality of rectors 150 is utilized as a single reactor 10 configured to detect the same one test item, the controller 54 may calculate the detection result of one test item on the basis of the detection result of several reactors 150 detected by the light receiving unit 59a.

Conversely, if a current test is interrupted because a malfunction or faulty operation occurs in the test device, the memory according to the exemplary embodiment may store information related to a current test step.

For example, if the supply of power applied to the test device is suddenly interrupted and the current test is also interrupted, the controller may store information related to the current test step in the memory. In this case, the test device is powered off, and the test device is powered on by the auxiliary power supply installed therein, so that the controller may store information related to the current test step in the memory. There is a need for the auxiliary power-supply unit to provide only sufficient power needed for storing information related to the test step.

The test step may be predetermined and stored to be appropriate for categories of the test devices or categories of the reactors, and information regarding the test step may be stored in the tag of the reactor so that the test device can read the test step.

Information stored in the memory may indicate any one or more of various parameters related to the current test step. For example, information as to which step from among all steps is executed, information as to how much time is taken to execute the corresponding test step, and information as to how much time is taken to drive the rotary drive unit at a predetermined rotation speed may be stored in the memory. For example, information indicating that the seventh step from among twelve test steps is now in progress, information indicating that the heater is being driven for four minutes from among a total of ten minutes, and information indicating that the rotary drive unit rotates for one minute at 4500 rpm may be stored in the memory.

If the test device is powered off, the auxiliary power-supply unit may provide power to the controller and the memory, and the controller may store information related to the current test step in the memory. If power is supplied again to the test device, and if a user inputs a rebooting command to the test device, the controller may reboot the test device. If the test device is rebooted, the controller may recover the setting for continuing a performance of the test by resuming the corresponding test step using information related to the interrupted test step stored in the memory, and may continue the performance of the test by resuming the interrupted test step. For example, when the stopped seventh step is resumed, the heater is further driven for six minutes, and the rotary drive unit is driven for the remaining time other than one minute from among a total drive time in which the rotary drive unit is set to 4500 rpm.

Before the controller resumes the interrupted test step, the controller may display a message on the display unit so as to inquire about whether or not the interrupted test step can be resumed. The user may confirm the corresponding message, such that the interrupted test step may be resumed, all steps starting from an initial intermediate step may be performed, or a new test may also be performed.

In addition, when the test device is rebooted, the controller may determine whether the interrupted test step can be resumed again, before the performance of the interrupted test is continued. Due to characteristics of the test step, it may be difficult for a particular test step to be resumed after the test step has begun, and power may be suddenly interrupted during execution of the test step. Information as to which step from among all test steps will be used may be prestored, and the controller may determine whether it is difficult for the interrupted step to be resumed on the basis of the prestored information. Although the controller determines the interrupted test step to be a difficult test step which has a difficulty with respect to a continuity of performance, the controller may display a message on the display unit so as to inquire about whether the interrupted test step will be resumed. There may be an error in decision of the controller, and the decision of the controller may be variable determined by the user, so that the operation for receiving user confirmation may be further carried out. The user may confirm the corresponding message, such that the interrupted test step may be resumed, all steps starting from an initial intermediate step may be performed, or a new test may also be performed as necessary. In addition, when the interrupted test step is resumed, the controller may perform the remaining test steps during a predetermined time calculated when a specific time consumed for rebooting is subtracted from a time consumed for performing the remaining test steps.

If the interrupted test step is resumed so that the test is completed, the controller may display the test result on the display unit in such a manner that the user can recognize the test result.

If a power supply for the test device is disrupted, and if other malfunctions occur in the test device, the current testing may be interrupted. In this case, since the test device receives power from the power supply, information regarding the test step may be stored in the memory without assistance of the auxiliary power received from the auxiliary power supply.

As described above, the memory may store information regarding the test step related to a specific point at which the test is interrupted. Alternatively, in another exemplary embodiment, if each test step is completed, the memory may automatically store information regarding each respective completed test step. For example, if the first test step is completed, the controller may store control information related to execution of the first test step in the memory. If the second test step is completed, the controller may store control information related to execution of the second test step in the memory.

If the current test is interrupted due to a malfunction of the test device, information related to test steps prior to the interrupted test step may be stored in the memory.

If the test is interrupted as described above, the controller may count a lapse of a predetermined time from the time of the interruption. If the test device operates again before a lapse of the predetermined time and the interrupted test step is performed, no problems may occur. If the predetermined time has elapsed subsequent to the interruption, the controller may reboot the test device. If the test device is rebooted, the controller may recover the setting needed for reperforming the test by using information related to previous test steps which were completed prior to commencement of the interrupted test step stored in the memory in such a manner that the test can be performed again from the previous test step with respect to the interrupted test step, and may then carry out the test step. For example, if the test is stopped at the seventh step, the sixth step stored in the memory is resumed, and the test step is carried out using control information related to the sixth step. The control information may exemplarily indicate that the heater is driven for six minutes and the rotary drive unit is driven for one minute at 4500 rpm.

Prior to execution of the previous test step with respect to the interrupted test step, the controller may display a message for confirming whether the interrupted test step will be resumed on the display unit. The user may confirm the corresponding message, the interrupted test step may be resumed, all steps starting from an initial intermediate step may be performed, or a new test may also be performed as necessary. If a command for resuming the interrupted test step is received, the test is performed again in the range from the previous test step with respect to the interrupted test step.

If the test device is rebooted, the controller may determine whether the interrupted test step can be resumed prior to continuing an execution of the interrupted test. According to characteristics of the test step, it may be difficult for some test steps to be resumed, and the test device may be interrupted during the execution of such a difficult test step. Information as to which step from among all test steps will be used may be prestored in the memory, and the controller may determine whether it is difficult to resume the interrupted step on the basis of the stored information. Although the controller determines that it is difficult for the interrupted test step to be resumed, the controller may display a message on the display unit so as to inquire about whether the interrupted test step will be resumed. There may be an error in decision of the controller, and the decision of the controller may be variably determined by the user, so that the operation for receiving user confirmation may be further carried out. The user may confirm the corresponding message, such that the interrupted test step may be resumed, all steps starting from an initial intermediate step may be performed, or a new test may also be performed as necessary. In addition, when the interrupted test step is resumed, the controller may perform the remaining test steps during a predetermined time calculated when a specific time consumed for rebooting is subtracted from a time consumed for performing the remaining test steps.

If the test starting from the previous step with respect to the interrupted test step is performed so that the test is completed, the controller may display the test result on the display unit in such a manner that the user can recognize the test result.

Figure 6:
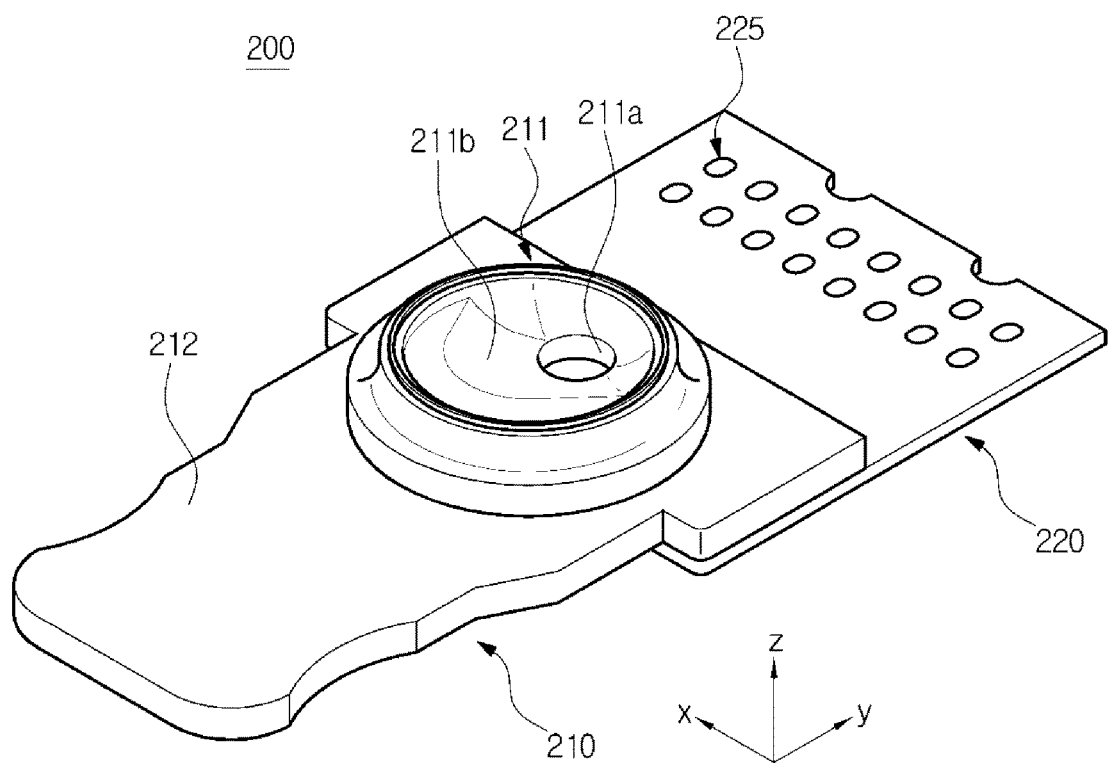
FIG. 6 is a schematic view illustrating a reactor, according to another embodiment.
Figure 7:
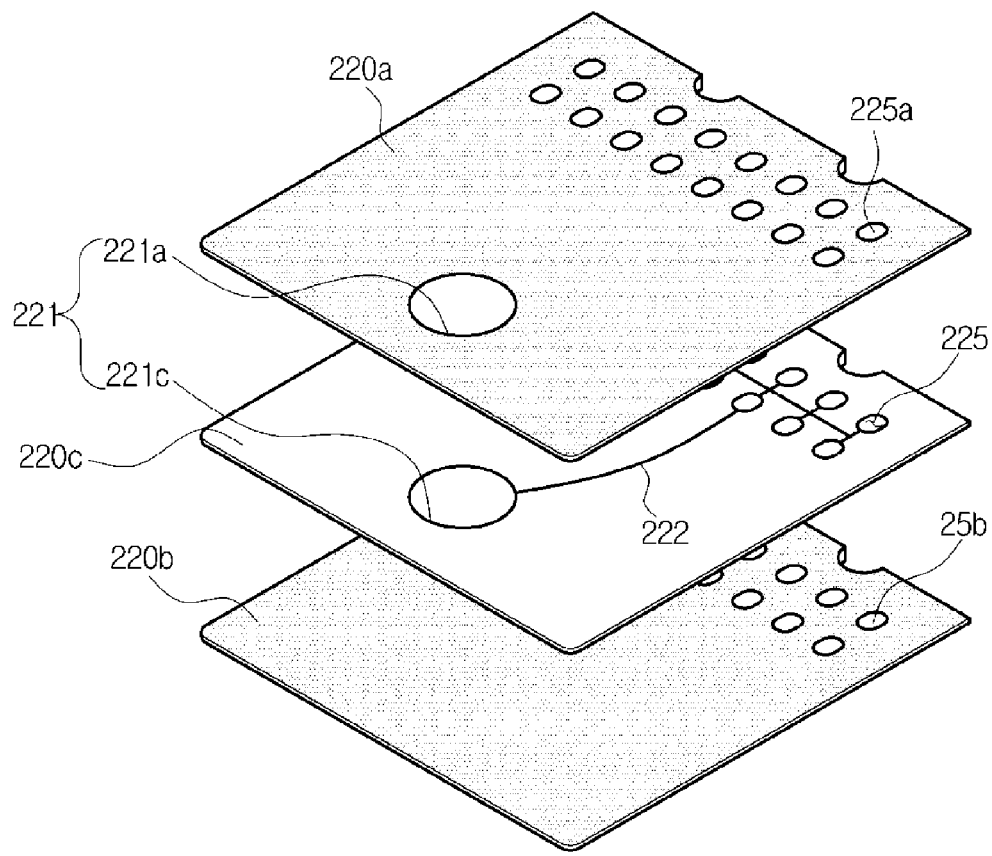
FIG. 7 is an exploded perspective view illustrating a testing unit shown in FIG. 6.

FIG. 6 is a schematic view illustrating the reactor, according to another exemplary embodiment. FIG. 7 is an exploded perspective view illustrating the testing unit shown in FIG. 6.

The reactor 200 may include a disc-type reactor 10 and a cartridge-type reactor 200.

As can be seen from FIG. 6, the reactor 200 may include a housing 210 configured for supporting the reactor 200 and a test unit (also referred to herein as a "test device" and/or as a "tester") 220 in which a reaction occurs by a combination of the fluid and the reagent.

The housing 210 may include a grasping unit (also referred to herein as a "grasping device" and/or as a "grasper") 212 grasped by the user and a fluid accommodating unit (also referred to herein as a "fluid accommodater") 211 for accommodating the fluid therein. The fluid accommodating unit 211 may include a hole 211a through which the fluid is inserted, and a supply auxiliary unit (also referred to herein as a "supply auxiliary device") 211b obliquely formed in such a manner that the fluid can be easily introduced into the hole 211a. A filter configured for removing blood cells from blood may be provided in the hole 211a when receiving the blood. The filter may include a porous polymer membrane formed of any of polycarbonate (PC), polyethersulfone (PES), polyethylene (PE), polysulfone (PS), polyarylsulfone (PASF), and/or the like. For example, in the case in which a blood sample is supplied, while blood passes through the filter, blood cells remain and only blood plasma or serum may be introduced into the test unit 220. A plurality of chamber-shaped reactors 225 in which fluid received through the fluid accommodating unit 211 is accommodated may be contained in the test unit 220. At least two reactors from among the plurality of reactors 225 provided at the test unit 220 may include a reagent for detecting the same one test item. Although not shown in the drawing, a tag needed to store ID information and a test method of the corresponding reactor 200 may be contained in the test unit.

Referring to FIG. 7, the test unit 220 may be formed by bonding three plates (220a, 220b, 220c) to one another. The three plates may include an upper plate 220a, a lower plate 220b, and a middle plate 220c. The upper plate 220a and the lower plate 220b may be printed with a light shielding ink, and may serve to protect the sample flowing into a reactor unit (also referred to herein as a "reactor device" and/or as a "reactor") 225 from external light.

The upper plate 220a and the lower plate 220b may take the form of films. The films, used to form the upper plate 220a and the lower plate 220b, may include any one or more selected from among a polyethylene film, such as a very low-density polyethylene (VLDPE) film, linear low density polyethylene (LLDPE) film, low-density polyethylene (LDPE) film, medium-density polyethylene (MDPE) film, high-density polyethylene (HDPE) film, etc., a polypropylene (PP) film, a polyvinylchloride (PVC) film, polyvinyl alcohol (PVA) film, polystyrene (PS) film, and/or a polyethylene terephthalate (PET) film.

The middle plate 220c of the test unit 220 may be a porous sheet, such as a cellulose sheet. Thus, the middle plate 220c may serve as a vent. The porous sheet may be formed of a hydrophobic material, or may be subjected to hydrophobic treatment, thus having no effect on movement of the sample.

The test unit 220 may include a sample introduction inlet 221 into which the sample is introduced, a channel 222 configured for facilitating movement of the introduced sample, and the reaction unit (also referred to herein as a "reactor component") 225 in which reaction between the sample and the reagent occurs.

As exemplarily shown in FIG. 7, when the test unit 220 has a triple-layered structure, the upper plate 220a may include an upper-plate hole 221a constructing the sample introduction inlet 221, and a portion 225a corresponding to the reactor unit 225 may be transparent.

A portion 225b of the lower plate 220b corresponding to the reactor unit 225 may be transparent. Providing the transparent portions (225a, 225b) corresponding to the reactor unit 225 facilitates obtaining a measurement of an optical property with regard to reaction occurring in the reactor unit 225.

The middle plate hole 221c constructing the sample introduction inlet 221 is formed at the middle plate 220c. When the upper plate 220a, the middle plate 220c, and the lower plate 220b are bonded to each other, the upper plate hole 221a and the middle plate hole 221c overlap each other, resulting in formation of the sample introduction inlet 221 of the test unit 220.

The reactor unit 225 is formed at a region opposite to the middle plate hole 121c from among the regions of the middle plate 220c. The reactor unit 225 may be formed by removing a given region, such as a circular region, a rectangular region, or the like, corresponding to the reactor unit 225 from among the region of the middle plate 220c, and the upper plate 220a, the middle plate 220b, and the lower plate 220c are bonded to each other, resulting in formation of the reactor unit 225.

In addition, the channel 222, which typically has a width within a range of 1 μm to 500 μm, is formed at the middle plate 220c and thus the sample introduced via the sample introduction inlet 221 may be moved to the reactor unit 225 by capillary pressure of the channel 222. However, the width of the channel 222 is merely an example that may be applied to the reactor 200, and exemplary embodiments are not limited thereto.

Figure 8:
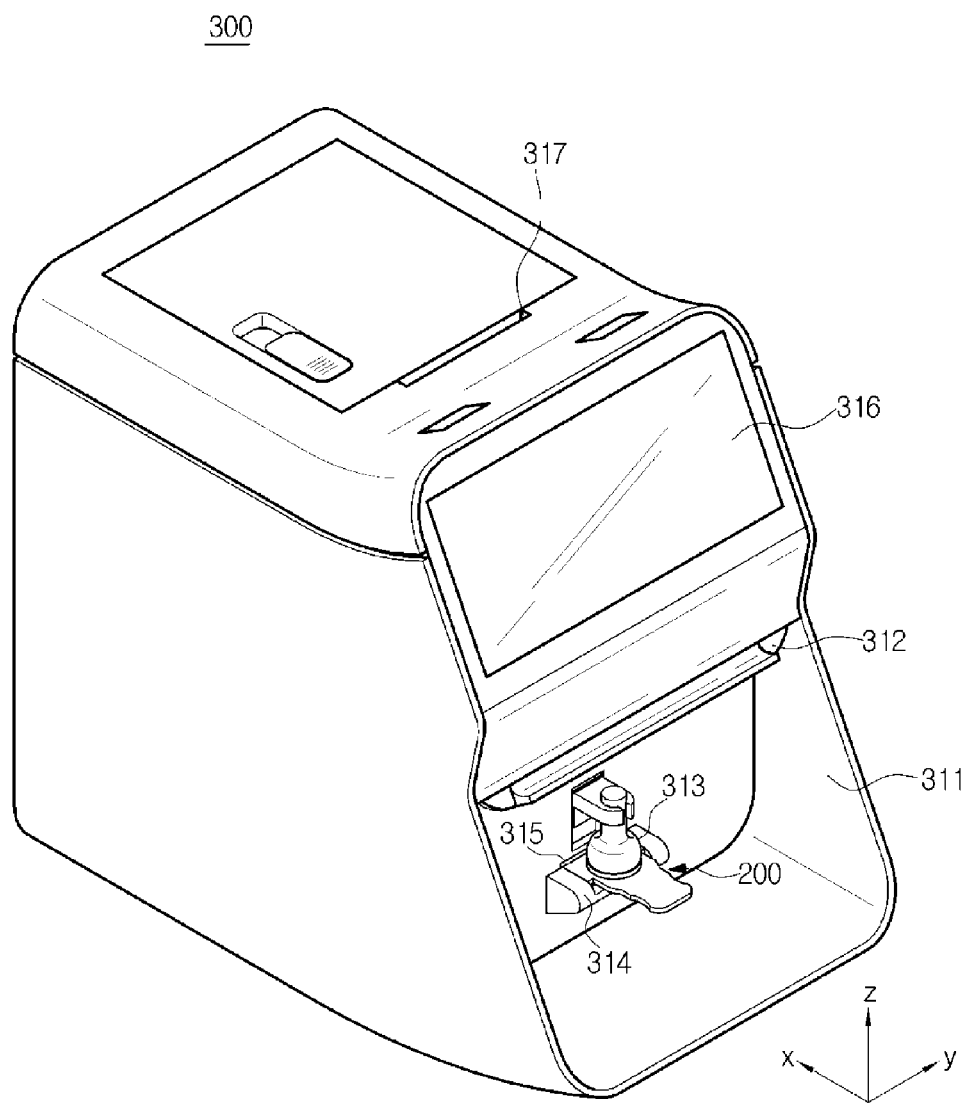
FIGS. 8 and 9 illustrate the external appearance of a test device, according to another exemplary embodiment.
Figure 9:
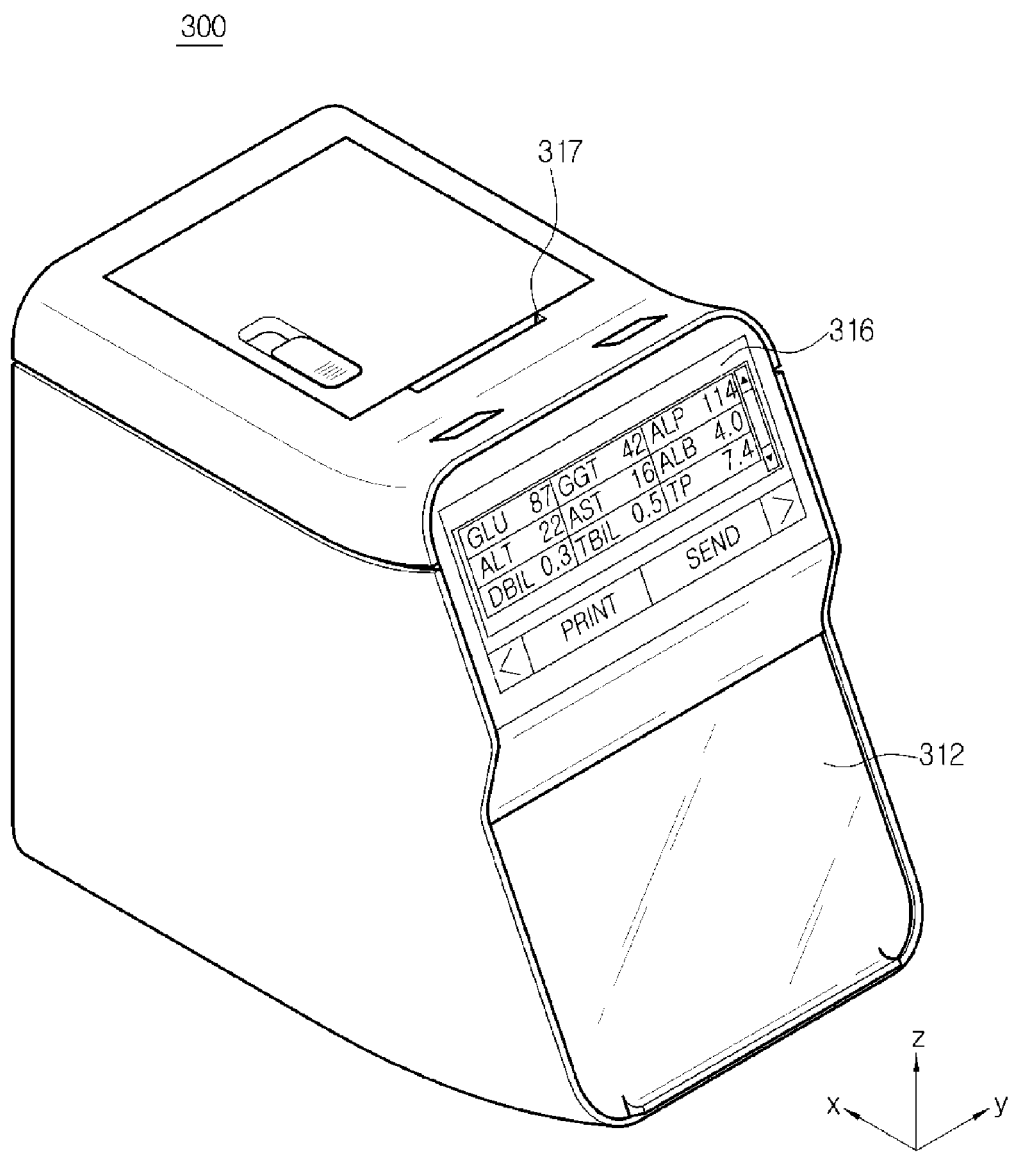
Figure 10:
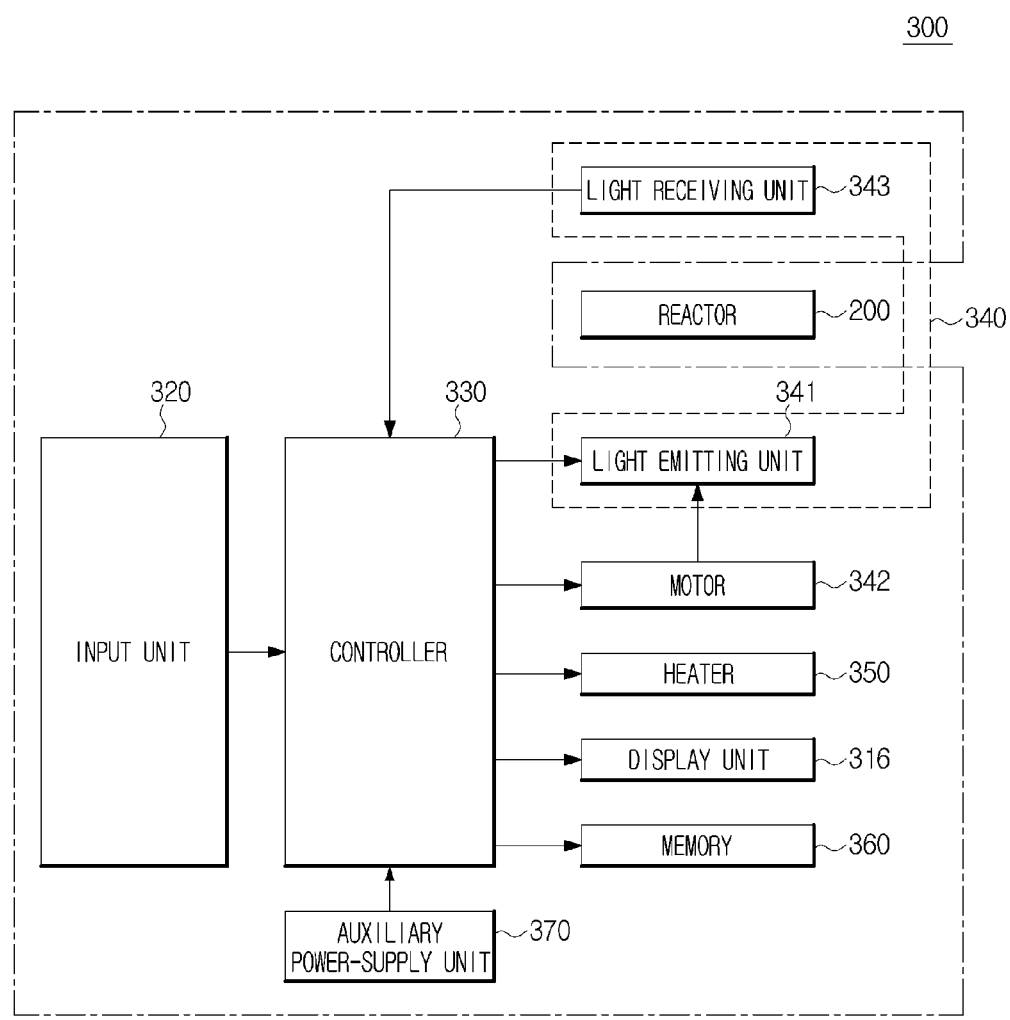
FIG. 10 is a block diagram illustrating a test device, according to another exemplary embodiment.

FIGS. 8 and 9 illustrate the external appearance of a test device, according to another exemplary embodiment. FIG. 10 is a block diagram illustrating a test device, according to another exemplary embodiment.

As can be seen from FIG. 8, the reactor 200 is inserted into the test device 300.

The test device 300 may include a mounting unit (also referred to herein as a "mounting component" and/or as a "mount") 311 to which the reactor 200 is mounted, a display unit (also referred to herein as a "display device" and/or as a "display") 316 for displaying the test result of the reactor 200, and an output unit (also referred to herein as an "output device") 317 for outputting the test result as a separate printed matter.

If a door 312 of the mounting unit 311 slides upward and the mounting unit 311 is opened, the mounting unit 311 is exposed. The reactor 200 is mounted to the mounting unit exposed by sliding of the door 312. In more detail, the reactor 200 may be inserted into a predetermined insertion groove 315 through which the test unit 220 of the reactor 200 can be inserted into the test unit 300.

As described above, the test unit 220 of the reactor 200 is inserted into the test device 300, and the housing 210 is supported by a housing support unit 314 so that the housing 210 is exposed to the outside. In addition, when a pressurization unit (also referred to herein as a "pressurizer") 313 pressurizes the fluid accommodating unit 211, introduction of a sample into the fluid accommodating unit 211 may be accelerated.

Meanwhile, when installation of the reactor 200 is completed, the door 312 is closed and a test of the reactor 200 starts as shown in FIG. 9.

As can be seen from FIG. 10, the test unit 300 may include a detection module 340 provided with a light emitting unit (also referred to herein as a "light emitting device" and/or as a "light emitter") 341 and a light receiving unit (also referred to herein as a "light receiving device" and/or as a "light receiver") 343; a motor 342 configured to move the detection module 340; a heater 350 configured to maintain or adjust a predetermined temperature of a space including the reactor; a memory 360 configured to store information related to a test progress; an auxiliary power-supply unit (also referred to herein as an "auxiliary power supplier" and/or as an "auxiliary power supply") 370 configured to provide auxiliary power in such a manner that the memory can store information related to a test step when powered off; an input unit (also referred to herein as an "input device") 320 configured to enable a user to input a command; and a controller 330 configured to control overall operations and functions of the test device 300 according to the command received via the input unit 320.

The light emitting unit 341 of the detection module 340 may include a surface light source having a large light emitting area so as to uniformly emit light to a certain region of the reactor 200. For example, a back light unit may be used as the light emitting unit 341.

Alternatively, the light emitting unit 341 may include any of a light source configured to turn on/off at a designated frequency, i.e., a semiconductor light emitting device, such as a light emitting diode (LED) or a laser diode (LD), or a gas discharge lamp, such as a halogen lamp or a xenon lamp.

The light receiving unit 343 of the detection module 340 may be configured to detect light irradiated from the light emitting unit 341 and transmitted or reflected by a sample accommodated in the reaction chamber of the reactor 200, and to generate an electrical signal according to the intensity of light. The light receiving unit 343 may include any of a depletion layer photo diode, an avalanche photo diode, or a photomultiplier tube. Alternatively, the light receiving unit 343 may include a complementary metal-oxide-semiconductor (CMOS) image sensor and/or a charge-coupled device (CCD) image sensor.

The light emitting unit 341 and the light receiving unit 343 may be provided opposite each other across the reactor 200, or both the light emitting unit 341 and the light receiving unit 343 may be provided above or below the reactor 200. In this exemplary embodiment, the light emitting unit 341 and the light receiving unit 343 may be provided opposite each other across the reactor 100.

The detection module may be configured to move along the arrangement direction of the reactor unit 225 so as to detect the reaction result of several reactor units 225, and power needed for movement of the detection module may be supplied from the motor 342 of the test device.

The controller 330 may be configured to control driving of the motor 342 so as to control movement of the detection module 340.

The intensity or wavelength of light irradiated from the light emitting unit 341 may be controlled according to instructions of the controller 330. The light receiving unit 343 may be configured to transmit an electrical signal, generated by detecting light, to the controller 330. The detection module 340 may further include an analog/digital "AD" converter configured to convert the detection result of the light receiving unit 343 into a digital signal, so that it may output a digital signal to the controller 330.

If the sample inserted into the reactor 200 moves to the reactor unit 225 which includes the reagent needed for detecting a test item, the detection module 340 may be configured to emit light to the reaction chamber under the control of the controller 330, to detect the light which propagates through the reaction chamber, and to transmit the detected light to the controller 330. The controller 330 may calculate absorbance on the basis of the transmitted detection result, so that the controller 330 may detect the presence or absence of a detection object or the density of the detection object.

If the test is completed, the display unit 316 of the test device 300 may display the test result thereon as shown in FIG. 9. The reactor 200 may include a plurality of reactor units (also referred to herein as "reactor components") 225 as shown in FIG. 6, and a plurality of test items can be detected from one reactor 200. If the plurality of test items has been detected, the display unit 316 may display the detection result of several test items as shown in FIG. 9.

As least two reactor units from among the plurality of reactor units 225 may also be configured to detect only one test item.

The controller 330 may move the detection module by controlling a driving operation of the motor 342, so that the light receiving unit 343 may detect the reactor unit 225.

If respective reactor units 225 are configured to detect different test items, the controller 330 may calculate the detection result of different test items on the basis of the detection result of the respective reactor units 225 detected by the light receiving unit 343.

If at least two reactor units 225 are configured to detect the same one test item, the controller 330 may calculate the detection result of one test item on the basis of the detection result of several reactor units 225 detected by the light receiving unit 343.

Meanwhile, if a malfunction occurs in the test device and the current test is interrupted, the memory of the test device according to another exemplary embodiment may store information regarding the current test step.

For example, if the supply of power applied to the test device is suddenly interrupted and the current test is also interrupted, the controller may store information related to the current test step in the memory. In this case, the test device is powered off, and the test device is powered on by the auxiliary power supply installed therein, so that the controller may store information related to the current test step in the memory. There is a need for the auxiliary power-supply unit to provide only power needed for storing information related to the test step.

The test step may be predetermined and stored to be appropriate for categories of the test devices or categories of the reactors.

Information stored in the memory may indicate any one or more of various parameters related to the current test step. For example, information as to which step from among all steps is executed, information as to how much time is taken to execute the corresponding test step, and information as to how much time is taken to drive the heater may be stored in the memory. For example, information indicating that the seventh step from among a total of twelve test steps is now in progress, and information indicating that the heater is being driven for four minutes from among a total of ten minutes may be stored in the memory.

If the test device is powered off, the auxiliary power-supply unit may provide power to the controller and the memory, and the controller may store information related to the current test step in the memory. If power is supplied again to the test device, and if a user inputs a rebooting command to the test device, the controller may reboot the test device up. If the test device is rebooted, the controller may recover the setting for continuing the performance of the corresponding test step using information related to the interrupted test step stored in the memory, and may resume the interrupted test step. For example, when the stopped seventh step is resumed, the heater is further driven for six minutes.

Before the controller resumes the execution of the interrupted test step, the controller may display a message on the display unit so as to inquire about whether or not the interrupted test step will be resumed. The user may confirm the corresponding message, such that the interrupted test step may be resumed, all steps starting from an initial intermediate step may be performed, or a new test may also be performed.

In addition, when the test device is rebooted, the controller may determine whether the interrupted test step can be resumed again, before the interrupted test is resumed. Due to characteristics of the test step, it may be difficult for a test step to be resumed, and power may be suddenly interrupted during execution of the test step. Information as to which step from among all test steps will be used may be prestored, and the controller may determine whether it is difficult for the interrupted step to be resumed on the basis of the prestored information. Although the controller determines the interrupted test step to be a difficult test step having difficulty in continuous execution, the controller may display a message on the display unit so as to inquire about whether the interrupted test step will be resumed. There may be an error in decision of the controller, and the decision of the controller may be variably determined by the user, so that the operation for receiving user confirmation may be further carried out. The user may confirm the corresponding message, such that the interrupted test step may be resumed, all steps starting from an initial intermediate step may be performed, or a new test may also be performed as necessary. In addition, when the interrupted test step is resumed, the controller may perform the remaining test steps during a predetermined time calculated when a specific time consumed for rebooting is subtracted from a time consumed for performing the remaining test steps.

If the interrupted test step is resumed so that the test is completed, the controller may display the test result on the display unit in such a manner that the user can recognize the test result.

If power supply for the test device is interrupted, and if other malfunctions occur in the test device, the current testing may be interrupted. In this case, since the test device receives power from the power supply, information regarding the test step may be stored in the memory without assistance of the auxiliary power received from the auxiliary power supply.

As described above, the memory may store information regarding the test step related to a specific point at which the test is interrupted. Alternatively, in another exemplary embodiment, if each test step is completed, the memory may automatically store information regarding the completed test step. For example, if the first test step is completed, the controller may store control information related to execution of the first test step in the memory. If the second test step is completed, the controller may store control information related to execution of the second test step in the memory.

If the current test is interrupted due to a malfunction of the test device, information related to test steps prior to the interrupted test step may be stored in the memory.

If the test is interrupted as described above, the controller may count a lapse of a predetermined time from the time of the interruption. If the test device operates again before a lapse of the predetermined time and the interrupted test step is successfully completed, no problems may occur. If the predetermined time has elapsed, the controller may reboot the test device. If the test device is rebooted, the controller may recover the setting needed for reperforming the test using information related to previous test steps of the interrupted test step stored in the memory in such a manner that the test can be performed again from the previous test step with respect to the interrupted test step, and may then carry out the test step. For example, if the test is interrupted at the $7^{th}$ step, the $6^{th}$ step stored in the memory is resumed, and the test step is carried out using control information related to the $6^{th}$ step. The control information may exemplarily indicate that the heater is driven for six minutes.

Prior to execution of the previous test step with respect to the interrupted test step, the controller may display a message for confirming whether the interrupted test step will be resumed on the display unit. The user may confirm the corresponding message, the interrupted test step may be resumed, all steps starting from an initial intermediate step may be performed, or a new test may also be performed as necessary. If a command for continuing the execution of the interrupted test step is received, the test is performed again in the range from the previous test step with respect to the interrupted test step.

In addition, if the test device is rebooted, the controller may determine whether the interrupted test step can be resumed prior to execution of the interrupted test. According to characteristics of the test step, it may be difficult for some test steps to be executed after an interruption without repeating the execution of the entire test step, and the test device may be stopped during the execution of such difficult test step. Information as to which step from among all test steps will be used may be prestored in the memory, and the controller may determine whether it is difficult to resume the interrupted step on the basis of the stored information. Although the controller determines that it is difficult for the interrupted test step to be executed after an interruption without repeating same, the controller may display a message on the display unit so as to inquire about whether the interrupted test step will be resumed. There may be an error in decision of the controller, and the decision of the controller may be variably determined by the user, so that the operation for receiving user confirmation may be further carried out. The user may confirm the corresponding message, such that the interrupted test step may be resumed, all steps starting from an initial intermediate step may be performed, or a new test may also be performed as necessary. In addition, when the interrupted test step is resumed, the controller may perform the remaining test steps during a predetermined time calculated when a specific time consumed for rebooting is subtracted from a time consumed for performing the remaining test steps.

If the test starting from the previous step with respect to the interrupted test step is performed so that the test is completed, the controller may display the test result on the display unit in such a manner that the user can recognize the test result.

Figure 11:
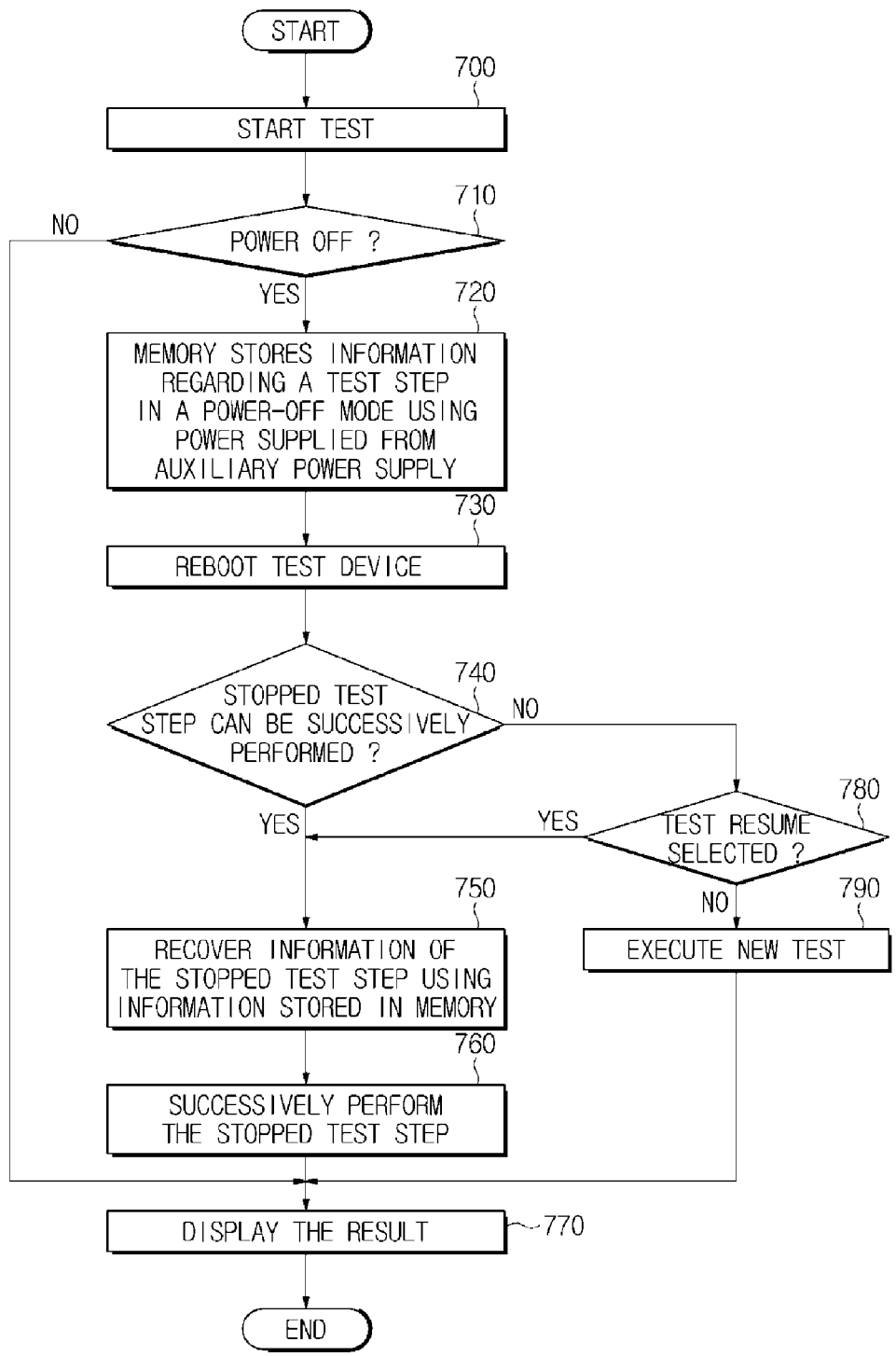
FIGS. 11 and 12 are flowcharts illustrating a method for controlling the test device, according to exemplary embodiments.
Figure 12:
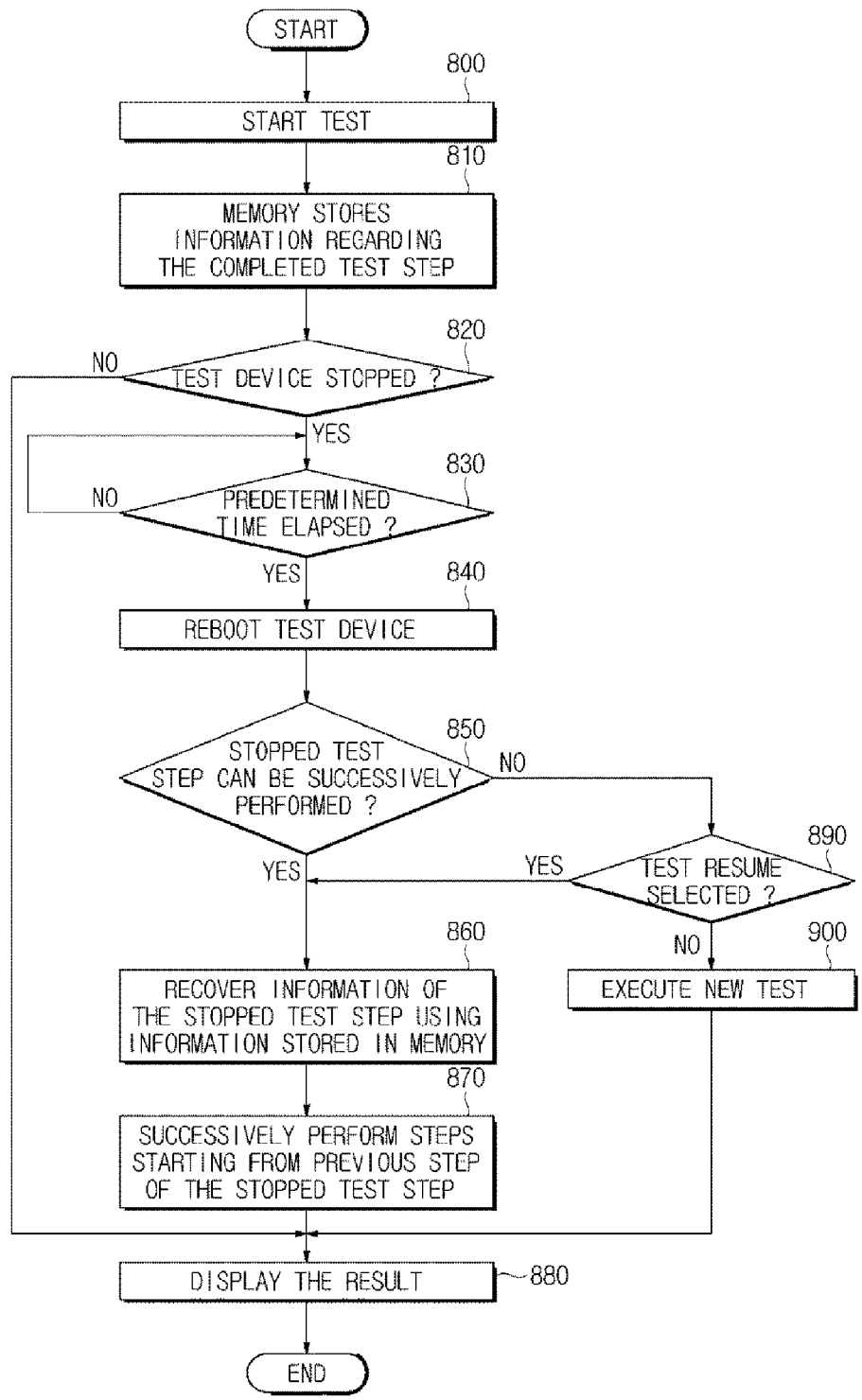

FIGS. 11 and 12 are flowcharts illustrating a method for controlling the test device, according to exemplary embodiments. For convenience of description and better understanding of the exemplary embodiments, the disc-type reactor will hereinafter be used as an example of the reactor, and the test device for testing the disc-type reactor will hereinafter be used as an example of the test device.

Referring to FIG. 11, a test starts in operation 700, and the test device is powered off in operation 710. The memory may store information related to the test step when powered off upon receiving power from the auxiliary power supply in operation 720.

If a malfunction occurs in the test device and the current test is suddenly interrupted, the memory according to the exemplary embodiment may store information related to the current test step.

For example, if the supply of power applied to the test device is suddenly interrupted and the current test is also interrupted, the controller may store information related to the current test step in the memory. In this case, the test device is powered off, and the test device is powered on by the auxiliary power supply installed therein, so that the controller may store information related to the current test step in the memory. There is a need for the auxiliary power-supply unit to provide only power needed for storing information related to the test step.

The test step may be predetermined and stored to be appropriate for categories of the test devices or categories of the reactors, and information regarding the test step may be stored in the tag of the reactor so that the test device can read the test step.

Information stored in the memory may indicate any one or more of various parameters related to the current test step. For example, information as to which step from among all steps is executed, information as to how much time is taken to execute the corresponding test step, information as to how much time is taken to drive the heater may be stored in the memory, and information as to how much time is taken to drive the rotary drive unit at a predetermined rotation speed may be stored in the memory. For example, information indicating that the seventh step from among a total of twelve test steps is now in progress, information indicating that the heater is being driven for four minutes from among a total of ten minutes, and information indicating that the rotary drive unit rotates for one minute at 4500 rpm may be stored in the memory.

If the test device is powered off, the auxiliary power-supply unit may provide power to the controller and the memory, and the controller may store information related to the current test step in the memory.

If information regarding the test step when the test device is powered off is stored in the memory, the controller may reboot the test device in operation 730, and may determine whether the stopped test step can be resumed in operation 740. If it is determined that the stopped test step can be resumed, the controller may recover information regarding the stopped test step using information stored in the memory in operation 750, and may resume execution of the stopped test step in operation 760.

If power is supplied again to the test device, and if a user inputs a rebooting command to the test device, the controller may reboot the test device up. If the test device is rebooted, the controller may determine whether the stopped test step can be resumed again, before the performance of the stopped test is continued. Due to characteristics of the test step, it may be difficult for a test step to be resumed after an interruption, and power may be suddenly stopped during execution of the test step. Information as to which step from among all test steps will be used may be prestored, and the controller may determine whether it is difficult for the stopped step to be resumed on the basis of the prestored information.

If the test step can be resumed, the controller may recover the setting needed for continuing the execution of the corresponding test step using information related to the stopped test step stored in the memory in such a manner that the stopped test step can be resumed. For example, if the stopped seventh step is resumed, the heater is driven for six minutes, and the rotary drive unit is driven at 4500 rpm during the remaining time other than the driven time of one minute from among a total driven time.

If the stopped test step is a test step incapable of being resumed after an interruption, the controller may display a message for confirming whether the test will be resumed on the display unit. If the test resume is selected in operation 780, the interrupted test resumes execution. If the test resume is not selected in operation 780, a new test is performed in operation 790.

If it is difficult for the stopped test step to be resumed after an interruption, the controller may display a message on the display unit so as to inquire about whether or not the stopped test step will be resumed. The user may confirm the corresponding message, such that the stopped test step may be resumed, all steps starting from an initial intermediate step may be performed, or a new test may also be performed.

Although the controller determines the stopped test step to be a difficult test step having difficulty in resumption of execution after an interruption, the controller may display a message on the display unit so as to inquire about whether the stopped test step will be resumed. There may be an error in decision of the controller, and the decision of the controller may be variably determined by the user, so that the operation for receiving user confirmation may be further carried out.

If the test is completed, the controller may display the test result on the display unit in operation 770.

If the stopped test step is resumed so that the test is completed, the controller may display the test result on the display unit in such a manner that the user can recognize the test result.

Referring to FIG. 12, the test starts in operation 800. If each test step is completed, the memory may store information regarding the completed step in operation 810.

If power supply for the test device is interrupted, and if other malfunctions occur in the test device, the current testing may be temporarily stopped. In this case, since the test device receives power from the power supply, information regarding the test step may be stored in the memory without assistance of the auxiliary power received from the auxiliary power supply.

As described above, the memory may store information regarding the test step related to a specific point at which the test is stopped. Alternatively, in another exemplary embodiment, if each test step is completed, the memory may automatically store information regarding the completed test step. For example, if the first test step is completed, the controller may store control information related to execution of the first test step in the memory. If the second test step is completed, the controller may store control information related to execution of the second test step in the memory. If the current test is stopped due to a malfunction of the test device, information related to test steps prior to the stopped test step may be stored in the memory.

If the test device stops in operation 820 and a predetermined time has elapsed from the time of interruption in operation 830, the controller may reboot the test device in operation 840. It is determined whether the stopped test step can be resumed in operation 850. If the stopped test step can be resumed, the controller may recover information regarding previous test steps with respect to the stopped test step using the information stored in the memory in operation 860, and may continue an execution of the steps starting from the previous step with respect to the stopped test step in operation 870.

If the test is stopped as described above, the controller may count a lapse of a predetermined time from the time of the interruption. If the test device operates again before a lapse of the predetermined time and the stopped test step is successfully executed, no problems may occur. If the predetermined time has elapsed after the interruption, the controller may reboot the test device. If the test device is rebooted, the controller may determine whether the stopped test step can be resumed, prior to continuing an execution of the stopped test. According to characteristics of the test step, it may be difficult for some test steps to be resumed after an interruption, and the test device may be temporarily stopped during the execution of such difficult test step. Information as to which step from among all test steps will be used may be prestored in the memory, and the controller may determine whether it is difficult to resume the execution of the stopped step on the basis of the stored information.

If the stopped test step can be resumed, the controller may recover the setting needed for re-testing steps starting from the previous test step with respect to the stopped test step using information related to the previous test step with respect to the stopped test step stored in the memory, such that the test step can be performed. For example, if the test is stopped at the seventh step, the sixth step stored in the memory is resumed, and the test step is carried out using control information related to the sixth step. The control information may exemplarily indicate that the heater is driven for six minutes and the rotary drive unit is driven for one minute at 4500 rpm.

If the stopped test step is a test step which is incapable of being resumed after an interruption, the controller may display a message for confirming whether the test will be resumed on the display unit. If the test resume is selected in operation 890, the execution of stopped test is continued. If the test resume is not selected in operation 890, a new test is performed in operation 900.

If it is difficult for the stopped test step to be resumed after an interruption, the controller may display a message on the display unit so as to inquire about whether or not the execution of the stopped test step will be resumed. The user may confirm the corresponding message, such that the stopped test step may be resumed, all steps starting from an initial intermediate step may be performed, or a new test may also be performed.

Although the controller determines the stopped test step to be a difficult test step having difficulty in continuing an execution after an interruption, the controller may display a message on the display unit so as to inquire about whether the stopped test step will be resumed. There may be an error in decision of the controller, and the decision of the controller may be variably determined by the user, so that the operation for receiving user confirmation may be further carried out.

If the test is completed, the controller may display the test result on the display unit in operation 880.

If the stopped test step is resumed so that the test is completed, the controller may display the test result on the display unit in such a manner that the user can recognize the test result.

As is apparent from the above description, although the test is temporarily stopped due to a malfunction of the test device, the test device according to the exemplary embodiments can continue the performance of the stopped test without execution of a new test, so that the test device can perform a test without replacement of the reactor such as a microfluidic device. As a result, the test device can prevent a waste of the reactor.

In addition, although the test is suddenly interrupted, the performance of the test can be continued after the interruption, resulting in increased stability of the test device.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. A test device for testing a biological material, comprising:
    a memory configured to store information which relates to progress of a test;
    a controller which, if the test is interrupted due to a malfunction of the test device, is configured to continue a performance of the interrupted test by using the information which relates to the progress of the test which is stored in the memory; and
    an auxiliary power supplier configured to provide the test device with auxiliary power when the test device is powered off,
    wherein the memory is further configured such that if the test device is powered off so that the test is interrupted, the information stored in the memory includes information which relates to a test step of a specific time at which the test is interrupted, by using power received from the auxiliary power supplier.

2. The test device according to claim 1, wherein:
    if a rebooting command is received, the controller is further configured to reboot the test device, and to continue the performance of the test by using the stored information which relates to the test step of the specific time at which the test is interrupted.

3. The test device according to claim 2, wherein the controller is further configured to continue the performance of the interrupted test during a test time calculated when a time consumed for rebooting is subtracted from a remaining test time.

4. The test device according to claim 2, wherein:
    the test step of the specific time at which the test is interrupted, is an interrupted test step, and
    after the test device is rebooted, the controller is further configured to determine whether the interrupted test step is a test step which is capable of being resumed, and to display a message for confirming whether the interrupted test step is to be resumed on a display of the test device, when the interrupted test step is not identical to the test step which is determined as being capable of being resumed.

5. The test device according to claim 4, wherein:
    if a resume command with respect to the interrupted test step is received in response to the displayed message, the controller is further configured to continue the performance of the test by using the stored information which relates to the test step at a test stoppage time point.

6. The test device according to claim 1, wherein when a predetermined test step is completed, the memory is further configured to store information which relates to the completed test step.

7. A test device for testing a biological material, comprising:
    memory configured to store information which relates to progress of a test; and
    a controller which, if the test is interrupted due to a malfunction of the test device, is configured to continue a performance of the interrupted test by using the information which relates to the progress of the test which is stored in the memory,
    wherein when a predetermined test step is completed, the memory is further configured to store information which relates to the completed test step, and
    wherein if the test device is interrupted and a predetermined time elapses after the interruption, the controller is further configured to reboot the test device, and to perform steps starting from a previously completed test step which was completed prior to the interruption of the test device, by using the information stored in the memory.

8. The test device according to claim 7, wherein:
after the test device is rebooted, the controller is further configured to determine whether a test step being performed at a time of the interruption is a test step which is capable of being resumed, and to display a message for confirming whether the interrupted test step is to be resumed on a display of the test device, when the interrupted test step is not identical to the test step which is determined as being capable of being resumed.

9. The test device according to claim 8, wherein:
if a resume command with respect to the interrupted test step is received in response to the message, the controller is further configured to perform steps starting from a previously completed test step which was completed prior to the interruption of the test device by using the information stored in the memory.

10. A method for controlling a test device configured to perform a test of a biological material, comprising:
if a test is interrupted due to a malfunction of the test device, storing information which relates to progress of the test; and
continuing a performance of the interrupted test by using the stored information,
wherein the storing the information which relates to the progress of the test comprises if the test device is powered off so that the test is interrupted, storing information which relates to a test step of a specific time at which the test is interrupted by using power received from an auxiliary power supplier.

11. The method according to claim 10, wherein the operation for continuing the performance of the interrupted test comprises:
continuing the performance of the interrupted test by using information which relates to a test step being performed at a test stoppage time point.

12. The method according to claim 10, wherein the storing the information which relates to the progress of the test includes comprises:
when a predetermined test step is completed, storing information which relates to the completed test step.

13. The method according to claim 10, wherein the operation for continuing the performance of the interrupted test comprises:
performing steps starting from a previously completed test step which was completed prior to the interruption of the test device by using the stored information.

14. A non-transitory computer-readable recording medium comprising a program configured to execute the method of claim 10.

15. A method for controlling a test device configured to perform a test of a biological material, comprising:
if a test is interrupted due to a malfunction of the test device, storing information which relates to progress of the test;
continuing a performance of the interrupted test by using the stored information;
rebooting the test device in response to receiving a rebooting command;
determining whether an interrupted test step is a test step which is capable of being resumed; and
if the interrupted test step is not identical to the test step which is determined as being capable of being resumed, displaying a message for confirming whether the interrupted test step is to be resumed, on a display of the test device.

16. The method according to claim 15, further comprising:
if a resume command with respect to the interrupted test step is received in response to the message, continuing the performance of the interrupted test by using information which relates to the test step being performed at a test stoppage time point and which is stored in a memory.

17. The method according to claim 15, wherein the operation for continuing the performance of the interrupted test comprises:
continuing the performance of the interrupted test during a test time calculated when a time consumed for rebooting is subtracted from a remaining test time.

18. The method according to claim 15, wherein the operation for continuing the performance of the interrupted test comprises:
continuing the performance of the interrupted test by using information which relates to a test step being performed at a test stoppage time point.

19. The method according to claim 15, wherein the storing the information which relates to the progress comprises:
when a predetermined test step is completed, storing information which relates to the completed test step.

20. The method according to claim 15, wherein the operation for continuing the performance of the interrupted test comprises:
performing steps starting from a previously completed test step which was completed prior to the interruption of the test device by using the stored information.

21. A non-transitory computer-readable recording medium comprising a program configured to execute the method of claim 15.

22. A method for controlling a test device configured to perform a test of a biological material, comprising:
if a test is interrupted due to a malfunction of the test device, storing information which relates to progress of the test;
continuing a performance of the interrupted test by using the stored information;
determining whether a predetermined time has elapsed after the test device was interrupted;
rebooting the test device if the predetermined time is determined as having elapsed;
determining whether a test step being performed at a time of the interruption is a test step which is capable of being resumed; and
if the interrupted test step is not identical to the test step which is determined as being capable of being resumed, displaying a message for confirming whether the interrupted test step is to be resumed on a display of the test device.

23. The method according to claim 22, further comprising:
if a resume command with respect to the interrupted test step is received in response to the message, performing steps starting from a previously completed test step which was completed prior to the interruption of the test device by using the information stored in a memory.

24. The method according to claim 22, wherein the operation for continuing the performance of the interrupted test comprises:
continuing the performance of the interrupted test during a test time calculated when a time consumed for rebooting is subtracted from a remaining test time.

25. The method according to claim 22, wherein the operation for continuing the performance of the interrupted test comprises:
   continuing the performance of the interrupted test by using information which relates to a test step being performed at a test stoppage time point.

26. The method according to claim 22, wherein the storing the information which relates to the progress comprises:
   when a predetermined test step is completed, storing information which relates to the completed test step.

27. The method according to claim 22, wherein the operation for continuing the performance of the interrupted test comprises:
   performing steps starting from a previously completed test step which was completed prior to the interruption of the test device by using the stored information.

28. A non-transitory computer-readable recording medium comprising a program configured to execute the method of claim 22.

* * * * *